US011447729B2

(12) United States Patent
Timmins

(10) Patent No.: US 11,447,729 B2
(45) Date of Patent: Sep. 20, 2022

(54) APPARATUS AND METHOD FOR BIOPROCESSING

(71) Applicant: GLOBAL LIFE SCIENCES SOLUTIONS USA LLC, Marlborough, MA (US)

(72) Inventor: Mark Robert Timmins, Chelmsford, MA (US)

(73) Assignee: GLOBAL LIFE SCIENCES SOLUTIONS USA LLC, Marlborough, MA (US)

( * ) Notice: Subject to any disclaimer, the term of this patent is extended or adjusted under 35 U.S.C. 154(b) by 462 days.

(21) Appl. No.: 16/229,670

(22) Filed: Dec. 21, 2018

(65) Prior Publication Data

US 2020/0199504 A1 Jun. 25, 2020

(51) Int. Cl.
*C12M 3/00* (2006.01)
*C12M 1/00* (2006.01)
*C12M 1/34* (2006.01)

(52) U.S. Cl.
CPC .............. *C12M 3/00* (2013.01); *C12M 23/34* (2013.01); *C12M 41/44* (2013.01)

(58) Field of Classification Search
CPC ........ C12M 23/34; C12M 29/10; C12M 3/00; C12M 41/44
See application file for complete search history.

(56) References Cited

U.S. PATENT DOCUMENTS

| 4,832,848 | A | * | 5/1989 | Velebil | ................. | C02F 3/1247 |
| | | | | | | 210/617 |
| 6,544,788 | B2 | | 4/2003 | Singh | | |
| 9,255,243 | B2 | | 2/2016 | Wilson et al. | | |
| 2016/0145563 | A1 | | 5/2016 | Berteau et al. | | |
| 2017/0226462 | A1 | | 8/2017 | Wu | | |
| 2018/0057784 | A1 | | 3/2018 | Wang et al. | | |

OTHER PUBLICATIONS

International Search Report issued in corresponding PCT Application No. PCT/EP2019/086087 dated Mar. 10, 2020.

* cited by examiner

*Primary Examiner* — Lydia Edwards
(74) *Attorney, Agent, or Firm* — Grogan, Tuccillo & Vanderleeden, LLP

(57) ABSTRACT

A bioreactor vessel incudes a first compartment configured to receive a suspension comprising cells and a cell culture medium, for use in a cell processing operation, a second compartment for receiving an overflow of the cell culture medium from the first compartment, and an overflow separating the first compartment from the second compartment, the overflow being configured to maintain a level of the cell culture medium in the first compartment.

16 Claims, 5 Drawing Sheets

APPARATUS AND METHOD FOR BIOPROCESSING

BACKGROUND

Technical Field

Embodiments of the invention relate generally to bioprocessing apparatuses, systems and methods and, more particularly, to a bioreactor vessel and perfusion methods for a bioreactor vessel.

DISCUSSION OF ART

A variety of vessels, devices, components and unit operations are known for carrying out biochemical and/or biological processes and/or manipulating liquids and other products of such processes. Such biological processes may be used in, for example, the manufacture of cellular immunotherapies such as chimeric antigen receptor (CAR) T cell therapy, which redirects a patient's T cells to specifically target and destroy tumor cells. As is known in the art, the manufacture of cellular immunotherapies, such as CAR T cell therapy, may involve the extraction, activation, genetic modification, culture and expansion of cells in one or more bioreactor vessels.

Recent advancements in the manufacture of cellular immunotherapies have provided for the automation of many bioprocess steps. For example, activation, genetic modification and/or expansion of a population of cells may be carried out in an automated or quasi-automated manner without substantial human operator intervention. U.S. Provisional Application Ser. No. 62/736,144, which is hereby incorporated by reference herein in its entirety, discloses one example of a functionally-closed, automated system for cell culturing and, in particular, for use in the manufacture of a CAR T cell therapy. As disclosed therein, fluid transfer and handling, including the addition and removal of various cell cultures, inoculum, media, reagents, rinse buffers, etc. into and from the bioreactor vessel(s) at precise volumes, rates, times and durations is an important consideration in many bioprocess operations, including in the production of cells and cell-derived products for a variety of applications.

Perfusion, also referred to as continuous cell culture, is one type of fluid transfer process that is often utilized in static culture vessels as well as stirred tank and rocking bioreactors, such as during the cell expansion phase. Perfusion involves providing a steady source of fresh cell culture media to the bioreactor vessel and constant removal of waste products and/or spent (i.e., used) media from the bioreactor vessel. Traditionally, media perfusion involves the use of two coordinated pumps, one pulling the 'spent' media to waste at some defined rate and another supplying fresh replacement media at the same rate. It is essential to the operation of such a system that the two net rates of fluid addition be equal. Existing systems, however, require the use of some type of reactive control logic to ensure that equivalent volumes of media are simultaneously added and removed from the bioreactor vessel, making the system, as a whole, costlier, more complex and more difficult to operate than other systems employing different culturing techniques. In addition, a filter on the perfusion-out line is often necessary to ensure that the cells are retained in the bioreactor vessel during perfusion, and to prevent the cells from being aspirated to waste.

In view of the above, there is a need for a bioreactor vessel that allows for perfusion to be carried out without the need for complex sensors and control logic that have heretofore been necessary to ensure equivalent volumes of media are simultaneously added and removed from the bioreactor vessel, and a method of perfusion utilizing such a bioreactor vessel that is simpler than existing methods.

BRIEF DESCRIPTION

In an embodiment, a bioreactor vessel includes a first compartment configured to receive a suspension comprising cells and a cell culture medium, for use in a cell processing operation, a second compartment for receiving an overflow of the cell culture medium from the first compartment, and an overflow separating the first compartment from the second compartment, the overflow being configured to maintain a level of the cell culture medium in the first compartment.

In another embodiment, a bioprocessing system includes a bioreactor vessel having a bottom, a top and a plurality of sidewalls, the bottom, the top and the plurality of sidewalls defining an interior chamber, a weir extending upwardly from the bottom, the weir and at least one sidewall of the plurality of sidewalls defining a first compartment within the interior chamber for holding a suspension comprising cells suspended in a cell culture medium, and a second a compartment within the interior chamber for receiving an overflow of used culture medium from the first compartment, an inlet associated with the first compartment, and an outlet associated with the second compartment. The bioprocessing system further includes a first pump in fluid communication with the inlet for pumping additional cell culture medium from a media reservoir to the first compartment of the bioreactor vessel through the inlet. The outlet is configured to allow for egress of used cell culture medium from the second compartment simultaneously or near simultaneously with the pumping of the additional cell culture medium to the first compartment.

In yet another embodiment, a method for bioprocessing includes the steps of, in a first compartment of a bioreactor vessel containing a suspension comprising cells suspended in a cell culture medium, introducing additional cell culture medium to simultaneously or near simultaneously cause used cell culture medium from the first compartment to exit the first compartment, wherein a substantially constant volume is maintained within the first compartment as the additional cell culture medium is introduced.

DRAWINGS

The present invention will be better understood from reading the following description of non-limiting embodiments, with reference to the attached drawings, wherein below.

DETAILED DESCRIPTION

Figure 1:
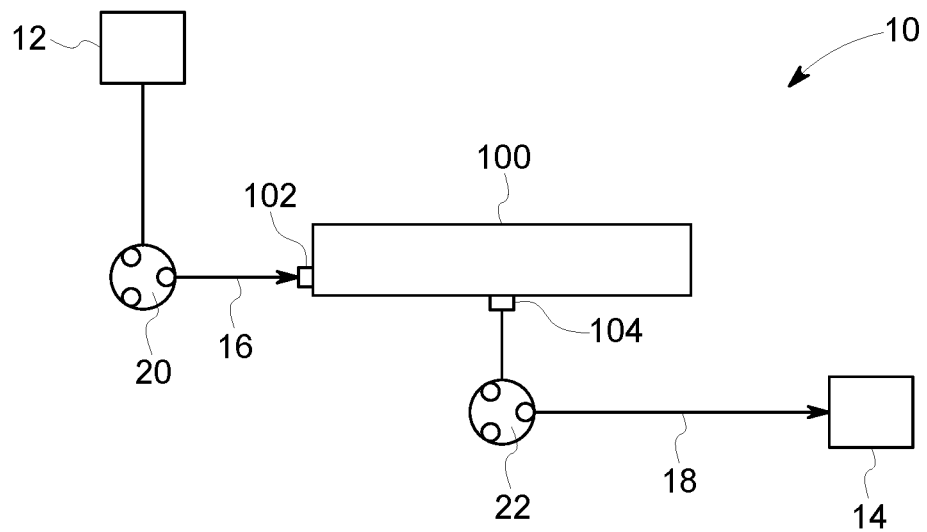
FIG. 1 is a schematic illustration of a bioprocessing system according to an embodiment of the invention.

Reference will be made below in detail to exemplary embodiments of the invention, examples of which are illustrated in the accompanying drawings. Wherever possible, the same reference characters used throughout the drawings refer to the same or like parts.

As used herein, "fluidly coupled" or "fluid communication" means that the components of the system are capable of receiving or transferring fluid between the components. The term fluid includes gases, liquids, or combinations thereof. As used herein, "operatively coupled" refers to a connection, which may be direct or indirect. The connection is not necessarily a mechanical attachment. As used herein, "weir" means a wall that extends upwardly from a bottom surface of the bioreactor vessel but which does not extend all the way to the top surface of the bioreactor vessel, such that fluid is permitted to flow or spill over the top edge of the weir. The term "overflow" is used herein to refer to any structure that allows for the passive transfer of fluid from one compartment or area of the bioreactor to another (or an area outside the bioreactor), and may encompass a weir or wall, an outlet, or a port. As used herein, "static bioreactor vessel" means a bioreactor vessel within which cells are processed under static conditions, i.e., without substantial movement of the bioreactor vessel itself, or agitation or rocking of the contents therein.

While embodiments of the invention are described herein in connection with the manufacture of biotherapeutic applications such as the manufacture of cell therapies and monoclonal antibodies, the invention is not so limited in this regard. In particular, it is contemplated that the bioreactor vessel of the invention may be utilized in any bioprocessing operations such as, for example, cell culturing, cell processing and/or cell expansion.

Embodiments of the invention are directed to bioreactor vessels that allow for used cell culture medium to be removed, and the depth of the medium and cell suspension to be controlled, without the use of a perfusion filter and/or active control logic coordinating input and output pumps. In an embodiment, a bioreactor vessel includes a first compartment configured to receive a suspension comprising cells suspended in a cell culture medium, for use in a cell processing operation, a second compartment for receiving an overflow of fluid from the first compartment, and a weir laterally separating the first compartment from the second compartment. As additional cell culture medium is added to the first compartment, used culture medium overflows over the top of the weir and into the second compartment to maintain a constant volume of fluid in the first compartment.

With reference to FIG. 1, a schematic illustration of a portion 10 of a bioprocessing system configured for continuous cell culturing, or perfusion, is shown. The bioprocessing system may generally be configured in accordance with any one of a variety of bioprocessing systems known in the art, such as the bioprocessing system disclosed in U.S. Provisional Application Ser. No. 62/736,144. In particular, the bioprocessing system includes, at minimum, a bioreactor vessel 100 having an inlet 102 configured for fluid coupling to a media source 12, and an outlet 104 configured for fluid coupling to a waste or collection reservoir 14 through first and second fluid transfer lines 16, 18, respectively. A first pump 20 along the first fluid transfer line 16 is utilized to pump a fluid, e.g., culture media, from the media source 12 to the bioreactor vessel 100 through inlet 102, and a second pump 22 along the second fluid transfer line 18 is utilized to pump fluid from the bioreactor vessel 100 to the waste or collection reservoir 14. For example, portion 10 of the bioprocessing system may be configured and utilized in a perfusion process whereby fresh cell culture medium is pumped to the bioreactor vessel 100 from the media reservoir 12 using the first pump 20, and spent/used medium removed from the bioreactor vessel 100 and pumped to waste 14 using second pump 22.

Figure 2:
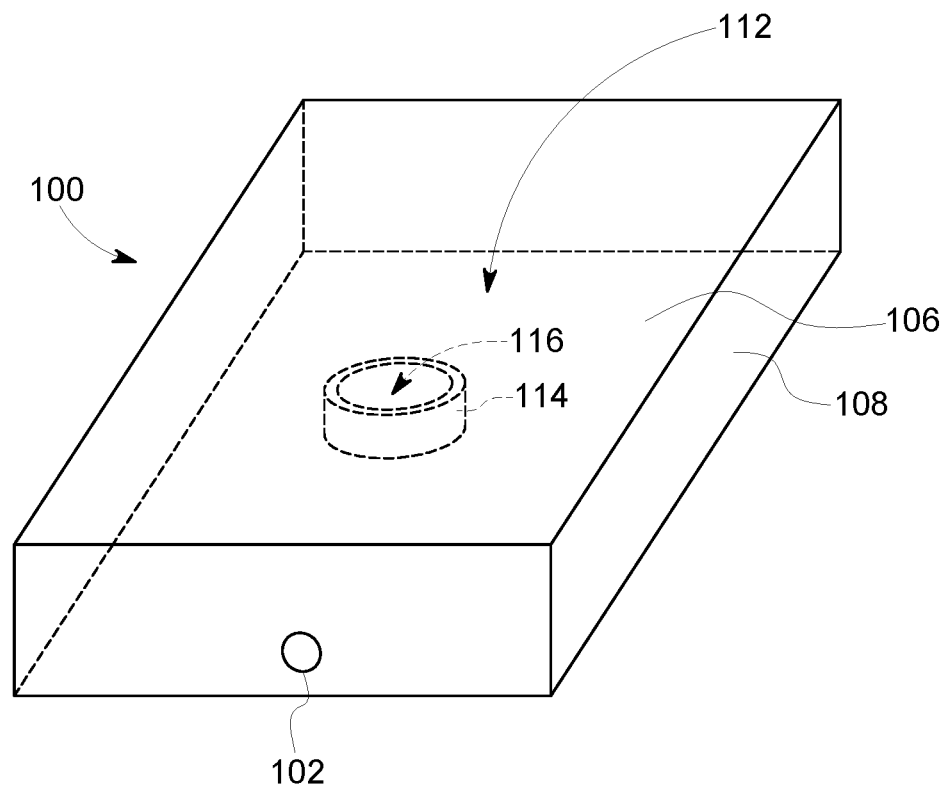
FIG. 2 is a perspective view of a bioreactor vessel of the bioprocessing system of FIG. 1, according to an embodiment of the invention.
Figure 3:
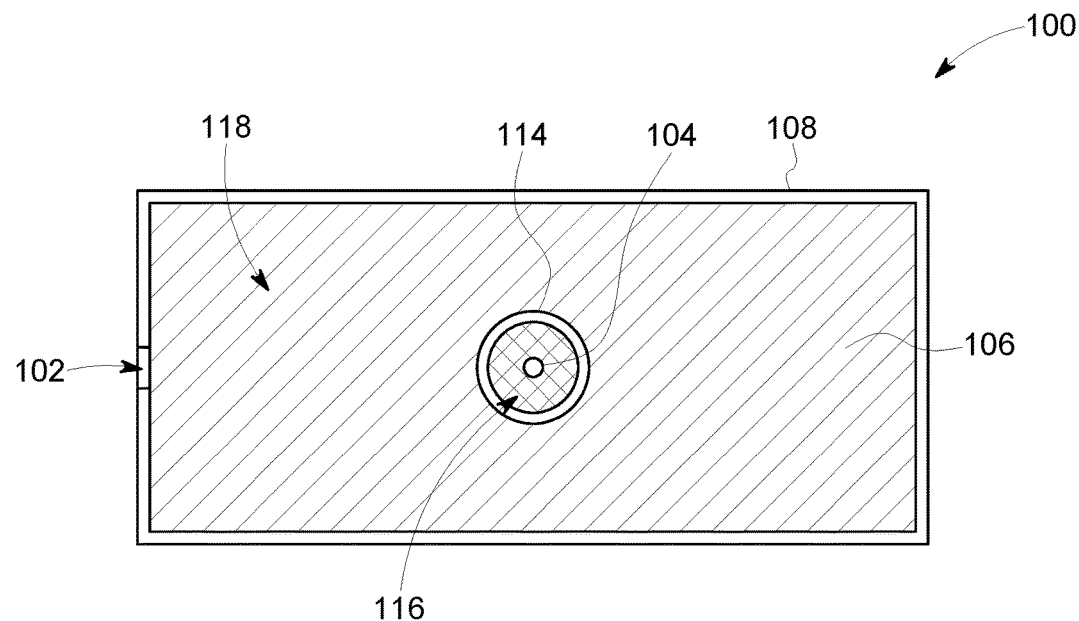
FIG. 3 is a top plan view of the bioreactor vessel of FIG. 2.
Figure 4:
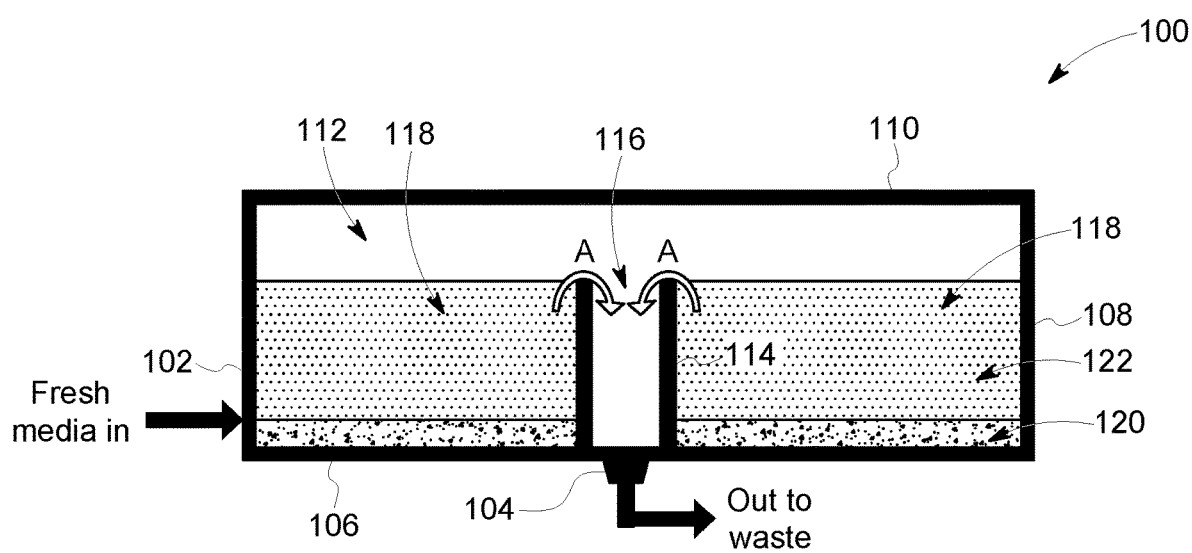
FIG. 4 is a side, cross-sectional view of the bioreactor vessel of FIG. 2.

Turning now to FIGS. 2-4, more detailed views of the bioreactor vessel 100 according to an embodiment of the invention are shown. In an embodiment, the bioreactor vessel 100 is a static bioreactor vessel having a bottom 106, a plurality of sidewalls 108 and a top 110 defining an interior chamber 112 therebetween. The interior chamber 112 is configured to receive a cell population for use in a bioprocessing operation (such as, for example, cell culturing, cell processing and/or cell expansion). In an embodiment, at least one of the bottom 106, top 110 and sidewalls 108 is formed from a gas-permeable, liquid impermeable material. In an embodiment, the bottom 106 of the vessel 100 is formed from a gas permeable material. The gas permeable material allows oxygen and/or other gases used in the cell culturing process to diffuse through the vessel walls and into the cell culture media in the interior chamber 112. Correspondingly, carbon dioxide or other gases diffuse through the walls and out of the vessel 100.

As further shown in FIGS. 2-4, in an embodiment, the bioreactor vessel 100 includes one or more walls or weirs 114 that extend upwardly from the bottom 106 of the bioreactor vessel 100 and define an overflow space 116 within the interior chamber 112. The weir(s) 114 have a height that is less than a depth or height of the bioreactor vessel 100, such that a top edge of the weir(s) 114 is spaced from the top 110 of the bioreactor vessel 100. As best shown in FIG. 4, the overflow space 116 is laterally segregated from the remainder of the interior chamber 112, but is otherwise in fluid communication with the interior chamber 112 due to the fact that the weir does not extend all the way to the top 110 of the bioreactor vessel 100. The weir 114 therefore defines, within the interior chamber 112 and above the bottom surface 106, a first area or compartment 118 configured to receive a population of cells for carrying out a bioprocessing operation such as, for example, cell culturing, cell processing and/or cell expansion, and a second area or compartment (i.e., overflow space 116) for receiving used medium from the first compartment 118, as discussed hereinafter.

In an embodiment, the weir 114 may by generally circular in shape, in plan view, and defines a generally cylindrical overflow space or compartment 116, however other configurations are also possible without departing from the broader aspects of the invention. For example, the weir 114 may have almost any peripheral shape so long as the weir defines an overflow space that is laterally segregated from the remainder of the interior chamber 112. In an embodiment, the weir 114 may extend laterally across the bioreactor vessel 100 from one side to an opposing side. In any such configuration, and as best illustrated in FIGS. 2 and 3, the outlet 104 is in fluid communication with the second compartment 116 (e.g., the outlet 104 may be located in the bottom 106 of the bioreactor vessel 100 and surrounded by the weir 114). Put another way, the outlet 104 is associated with, or located within, the second compartment 116. The inlet 102, for its part, is located in the bottom 106 of the bioreactor vessel 100 or in one of the sidewalls 108 of the bioreactor vessel 100, and is associated with, or located in, the first compartment 118. For example, in one embodiment, the inlet 102 is located in a sidewall 108 of the bioreactor vessel 100 adjacent to the bottom 106. In an embodiment, the inlet 102 is located between about 2 millimeters and about 30 millimeters from the bottom 106 of the bioreactor vessel 100. In an embodiment, the inlet 102 is located approximately 1 centimeter from the bottom 106 of the bioreactor vessel 100.

In an embodiment, the area and/or volume of the first compartment 118 (which retains a suspension comprising a population of cells suspended in a cell culture medium) is substantially greater than the area and/or volume of the second compartment 116. By minimizing the area of the second compartment 116 with respect to the first compartment 118, the area within the bioreactor vessel 100 used for cell processing can be maximized.

With specific reference to FIG. 4, a bioprocessing operation, such as perfusion, can be carried out utilizing the bioreactor vessel 100. A suspension comprising a population of cells 120 suspended in a cell culture medium 122 is added to the bioreactor vessel 100 in a manner known in the art, such as through inlet 102. The suspension is thus retained in the first compartment 118. As illustrated therein, the volume of the suspension contained within the first compartment 118 is defined by the height of the weir 114.

Before beginning perfusion of the cell culture, the cells 120 may be permitted to settle on the bottom 106 via gravitational force, as shown in FIG. 4. Once the cells 120 have settled, perfusion of the cells within the first compartment 118 may be performed by adding fresh medium through the inlet port 102 adjacent to the bottom 106 of the first compartment 118 using first pump 20 operating at a predetermined first rate (although it is envisioned that the fresh medium may also be drip-fed by gravity). As the height of the fluid within the first compartment 118 reaches the height of the weir 114, the addition of more fresh medium causes some of the spent/used medium near the top of the first compartment 118 to spill over the weir 114 and into the second compartment 116, as illustrated by arrows A. In a situation where the fluid level in the first compartment 118 is at its maximum (i.e., at a depth that corresponds to the height of the weir), adding any volume of additional cell culture medium at any rate will cause an equivalent volume of fluid (i.e., used cell culture medium) to spill over the weir 114 into the second compartment 116 at the same rate. The used medium that overflows into the second compartment 116 may then drain from the bioreactor vessel 100 through the outlet 104, such as under the force of gravity.

In other embodiments, however, the bioprocessing system 10 may employ second pump 22 to pull the used media from the second compartment 116 out of the bioreactor vessel 100. The second pump 22 may operate at a rate that is the same as, or different from, the rate of the first pump 20. Because the weir 114 dictates the maximum volume of fluid within the first compartment 118, the second pump 22 does not need to be run at the same time or the same rate as the first pump 20 in order to maintain a constant volume within the first compartment 118 (i.e., it does not need to be tied to process/perfusion control logic). In particular, as described above, adding additional cell culture medium to the first compartment 118 when it is at maximum capacity will automatically cause an equivalent volume of used medium to overflow into the second compartment 116, thereby maintaining the constant volume within the first compartment 118. This is in contrast to existing systems which require careful coordination between the inlet and outlet pumps to maintain a substantially constant working volume in the bioreactor vessel during perfusion. Indeed, as noted above, the second pump 22 may be entirely omitted from the system, if desired.

Removing used medium from the top of the first compartment 118 (passively by gravity) minimizes the risk of aspirating cells when pulling medium to waste, thereby obviating the need for a perfusion filter to retain the cells. This is particularly true when using low flow rates typically associated with perfusion, such as about 1 volume per day (e.g., for a culture volume of 500 mL, 1 volume per day perfusion would be 500 mL/day, or less than about 05 mL/min). Moreover, because the cells will settle by gravity, adding fresh medium adjacent to the bottom 106 near the cells 120 provides the cells 120 with the quickest access to fresh nutrients, while simultaneously or near simultaneously displacing spent/used medium upwards and over the weir 114 and into the second compartment 116 where it can then be removed from the bioreactor vessel 100 by gravity or by employing a second pump.

Figure 5:
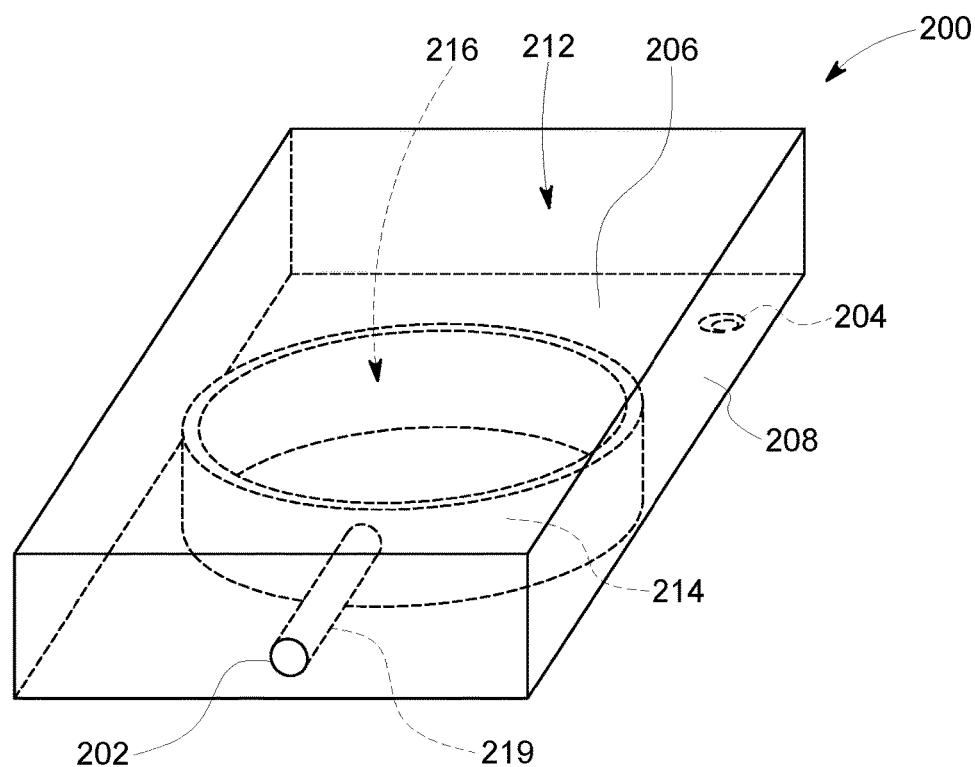
FIG. 5 is a perspective view of a bioreactor vessel of the bioprocessing system of FIG. 1, according to another embodiment of the invention.
Figure 6:
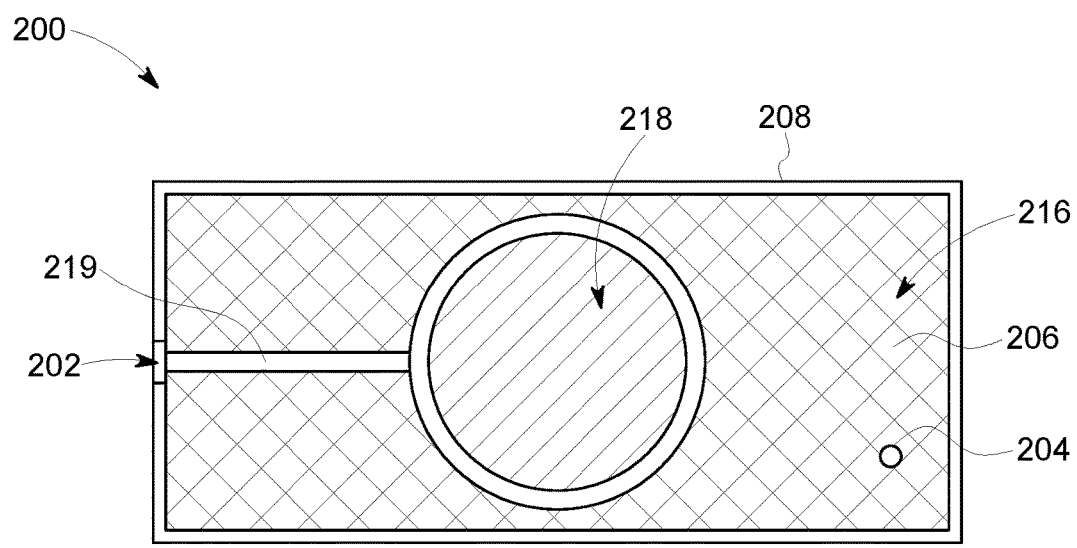
FIG. 6 is a top plan view of the bioreactor vessel of FIG. 5.
Figure 7:
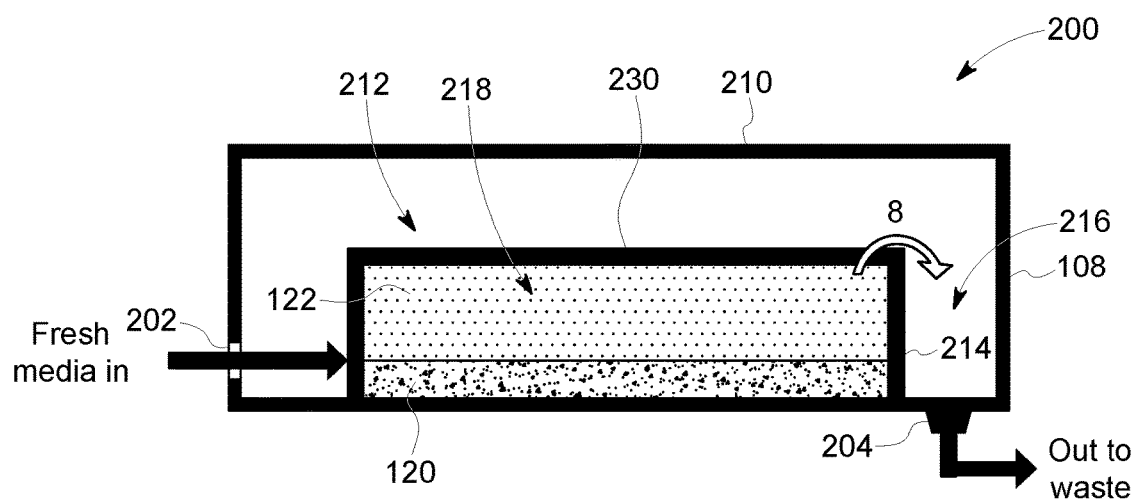
FIG. 7 is a side, cross-sectional view of the bioreactor vessel of FIG. 5.

Turning now to FIGS. 5-7, a bioreactor vessel 200 according to another embodiment of the invention is illustrated. The bioreactor vessel 200 is generally similar in configuration to the bioreactor vessel 100 of FIGS. 2-4, and includes a bottom 206, a plurality of sidewalls 208 and a top 210 defining an interior chamber 212 therebetween. Like the bioreactor vessel 100, bioreactor vessel 200 at least one of the bottom 206, top 210 and sidewalls 208 may be formed from a gas-permeable material. The bioreactor vessel 200 also includes one or more walls or weirs 214 that extend upwardly from the bottom 206 of the bioreactor vessel 200 and divide the interior chamber into a first compartment 218 for receiving a population of cells and culture medium, and a second compartment 216 defining an overflow space, the purpose of which has been hereinbefore described. As illustrated in FIGS. 5 and 6, however, rather than the first compartment and the cell culture therein surrounding the overflow space of the second compartment, first compartment 218 with the cell culture is surrounded on its outer periphery by the second, overflow compartment 216. In such an embodiment, the bioreactor vessel 200 may include a fluid passageway, e.g., a tube 219, fluidly connecting the inlet 202 with the interior space of the first compartment 218. As shown in FIGS. 5 and 6, the outlet 204 or drain port is associated with, i.e., located within, the second compartment 216.

As with the embodiment described above, the weir(s) 214 have a height that is less than a depth or height of the bioreactor vessel 200, such that a top edge of the weir(s) 214 is spaced from the top 1210 of the bioreactor vessel 200. As best shown in FIG. 7, the overflow space 216 is laterally segregated from the remainder of the interior chamber 212, but is otherwise in fluid communication with the interior chamber 212 due to the fact that the weir 214 does not extend all the way to the top 210 of the bioreactor vessel 200.

In use, a suspension comprising a population of cells 120 suspended in a cell culture medium 122 is added to the bioreactor vessel 100 in a manner known in the art, such as through inlet 202 and tube 219. The suspension is thus retained in the centrally-located first compartment 218. As illustrated in FIG. 7, the volume of the suspension contained within the first compartment 218 is defined by the height of the weir 214. Before beginning perfusion of the cell culture, the cells 120 may be permitted to settle on the bottom 206 via gravitational force, as shown in FIG. 7. Once the cells 120 have settled, perfusion of the cells within the first compartment 218 may be performed by adding fresh medium through the inlet port 202 adjacent to the bottom 206 of the first compartment 218 using first pump 20 operating at a predetermined first rate (although it is, again, envisioned that the fresh medium may also be drip-fed by gravity). As the height of the fluid within the first compartment 218 reaches the height of the weir 214, the addition of more fresh medium causes some of the spent/used medium near the top of the first compartment 218 to spill over the weir 214 and into the second compartment 216, as illustrated by arrow B. In a situation where the fluid level in the first compartment 218 is at its maximum (i.e., at a depth that corresponds to the height of the weir), adding any volume of additional cell culture medium at any rate will cause an equivalent volume of fluid (i.e., used cell culture medium) to spill over the weir 214 into the second compartment 216 at the same rate. The used medium that overflows into the second compartment 216 may then drain from the bioreactor vessel 100 through the outlet 104, such as under the force of gravity, or through operation of a second pump 22, as described above.

While the embodiments of the bioreactor vessels described herein describe such vessels as static culture vessels, it is contemplated that such bioreactor vessels may likewise be used as rocking bioreactor vessels. Where the bioreactor vessels are intended to be agitated and/or rocked during a cell processing operation, the bioreactor vessel may employ a membrane-like filter enclosing the top of the compartment that contains the cells. For example, as illustrated in FIG. 7, a cell-retaining membrane 230 may extend fully over the first compartment 218 to prevent the cells 120 contained therein from spilling out during rocking or agitating. In an embodiment, the cell retaining membrane 230 may allow for medium 122 to pass therethrough, but prevent the passage of cells 120. In other embodiments, the membrane 230 may be positioned lower, adjacent to the cells 120, which physically traps the cells 120 at the bottom of the first compartment. In yet other embodiments, the cells 120 may be retained at the bottom of the bioreactor vessel (and the first compartment thereof using surface-binding techniques (e.g., using adherent cells, binding the cells either directly to the bottom surface, or to microcarriers or the like with a much larger mass than a single cell to make the cells much less likely to stay in suspension). In this respect, a variety of bioreactor vessel configurations and techniques may be employed to retain the cells within the first compartment of the bioreactor vessel, allowing for perfusion using passive 'spillover' into the second compartment to be carried out without aspirating cells to waste. Absent the use of a retention filter, the embodiments of the invention described herein are well suited for static cultures in which the cells stay at the bottom of the bioreactor vessel, either by gravity or biochemical adherence. As discussed above, for cultures where the cells are in homogeneous suspension, a retention filter can be employed, as discussed above, to retain the cells during rocking, stirring, agitation and the like.

In some embodiments, the weir(s) may be selectively adjustable so that the depth, height, and/or volume of the suspension within the first compartment 118, 218 can be varied. In the embodiment of FIGS. 2-4, for example, the weir 114 may be configured as a tube or sleeve that is selectively extendable and retractable within the interior chamber 112. In such an embodiment, one or more sealing elements such as O-rings may be utilized to prevent medium or cells from leaking out of the bioreactor vessel through the interface between the bottom of the bioreactor vessel and the tube or sleeve. The use of an adjustable-height weir allows culture medium to be conserved throughout the cell culture process, decreasing the cost of operation of the bioreactor system 10, as a whole. For example, at the beginning of the cell expansion phase, the weir 114 may be retracted to a low position adjacent to the bottom 106 of the bioreactor vessel 100. As perfusion is carried out and the population of cells increases, the weir 114 may be extended or raised to allow for a greater volume of medium to be accommodated within the first compartment 118, to support cell growth.

In addition, in typical practice, cultures are batch fed (meaning additional fresh media is added without removing spent media) until the maximum desired culture volume is reached. This is often done for ease but has the disadvantage is that the cells are suspended with their own metabolic waste. By adjusting the height of the weir during the early stages of culture, the volume could be allowed to increase, to keep the cell density within an optimal range. Moreover, adjusting weir height could be extended beyond the initial culture period and through the duration of culture. In current practice, once the final volume is reached, perfusion is started and then increased over time as cell density rises in an attempt to keep the cells supplied with fresh media. This can result in extremely high cell densities (e.g., >25e6 per mL), which may be detrimental to cell health. By contrast, allowing the volume to continually increase by changing the height of the weir or spillover outlet (described below), the culture could be maintained at a more optimal cell density (e.g., 2e6 cells/mL).

In both situations described above, the absolute rate of perfusion would increase with the number of cells, and in that way the cost of media usage would be comparable. However, in the latter case, the perfusion rate could be held at a fixed relative rate (e.g., 1 volume per day). In a static culture, allowing the relative perfusion rate to increase could be detrimental to the objective of preventing the cells from being swept away by the perfusion flow, and thus raising the weir as cell number increases may be beneficial in retaining the cells.

Further to the discussion above regarding the peripheral shape of the weir and the ability to raise and lower the weir, in and embodiment, the weir may be configured such that the volume of the first compartment (e.g., first compartment 118) increases at a rate greater than linearly as the height of the weir is increased. For example, in an embodiment of FIG. 1, the weir 114 may have a funnel shape or angled sidewalls such that as the weir is raised, the volume of the first compartment 118 increases at a rate greater than linearly. In particular, a central weir (like that shown in FIG. 2) in the shape of a funnel or having angled walls allows the volume of the laterally adjacent first compartment 118 to be increased more and more upon each incremental raising of the weir (i.e., each successive incremental raising of the weir results in a greater increase in the volume of the first compartment 118 than each previous increment).

Figure 8:
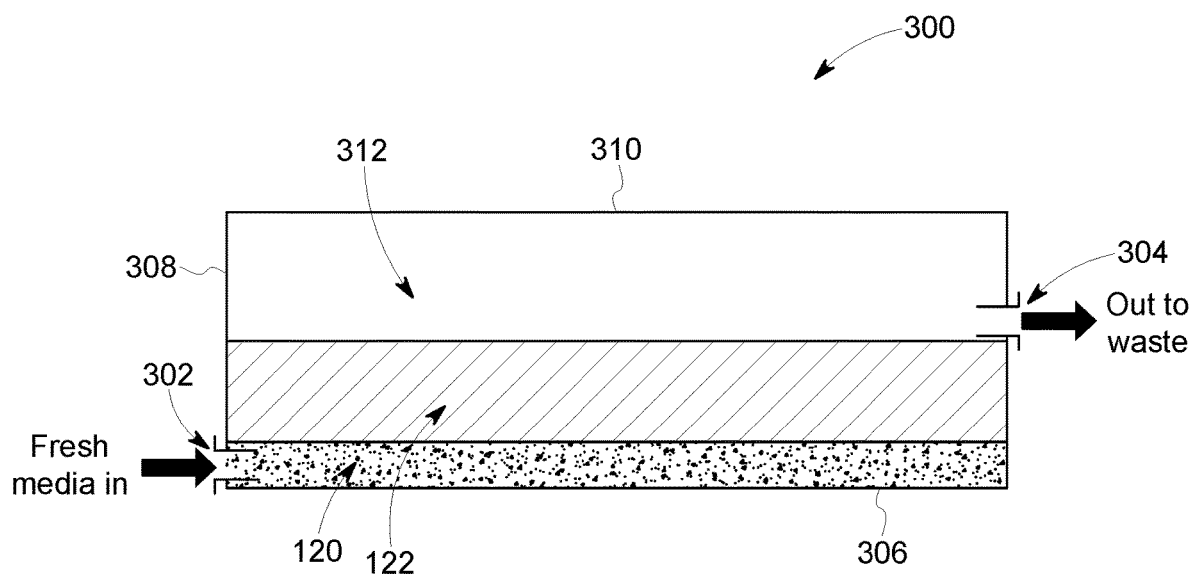
FIG. 8 is a cross-sectional view of a bioreactor vessel of the bioprocessing system of FIG. 1, according to another embodiment of the invention.

Turning to FIG. 8, in an embodiment, a bioreactor vessel 300 according to yet another embodiment of the invention is shown. The bioreactor vessel 300 includes a bottom 306, a plurality of sidewalls 308 and a top 310 defining an interior chamber 312 therebetween. The bioreactor vessel 300 also includes an inlet/port 302 located in one of the sidewalls 308 adjacent to the bottom 306. It is contemplated, however, that in some embodiments, the inlet 302 may be located in the bottom 306 or top 310 of the bioreactor vessel 300. As shown in FIG. 8, the bioreactor vessel 300 further includes an outlet/port 304 in one of the sidewalls 308 spaced a predetermined distance from the bottom 306. Similar to the weir in the embodiments described above, the height of the outlet 304 defines the maximum fluid height and volume of fluid within the bioreactor vessel 300.

In use during a perfusion process, a suspension comprising cells 120 suspended in a cell culture medium 122 is added to the interior chamber of the bioreactor 300. Additional cell culture medium is added to the bioreactor vessel 300 in the manner hereinbefore described, such as using first pump 20. As the additional cell culture medium is added, used medium exits the vessel 300 through the outlet in a passive manner (with or without using an independent second pump). As illustrated in FIG. 8, therefore, the height of the outlet 304 can be utilized to maintain the volume of fluid at a given value while controlling only the inflow rate of additional culture medium. In an embodiment, a perfusion filter may be utilized in the outlet or outlet tubing to retain the cells 120 in the bioreactor vessel.

While FIG. 8 shows the outlet 304 in the sidewall 308 of the bioreactor vessel 300, it is contemplated that the outlet may also be provided in the top of the vessel and used in conjunction with a siphon tube that extends downwardly towards the bottom 306 of the bioreactor vessel 300, the distal end of which can be selectively adjusted to be a desired distance from the bottom 306. In such embodiment, the distance of the distal end of the siphon tube from the bottom 306 defines the maximum media height within the bioreactor vessel 300. These concepts can be applied to stirred tank bioreactors, enabling perfusion to be carried out without active control or monitoring of used medium removal.

Figure 9:
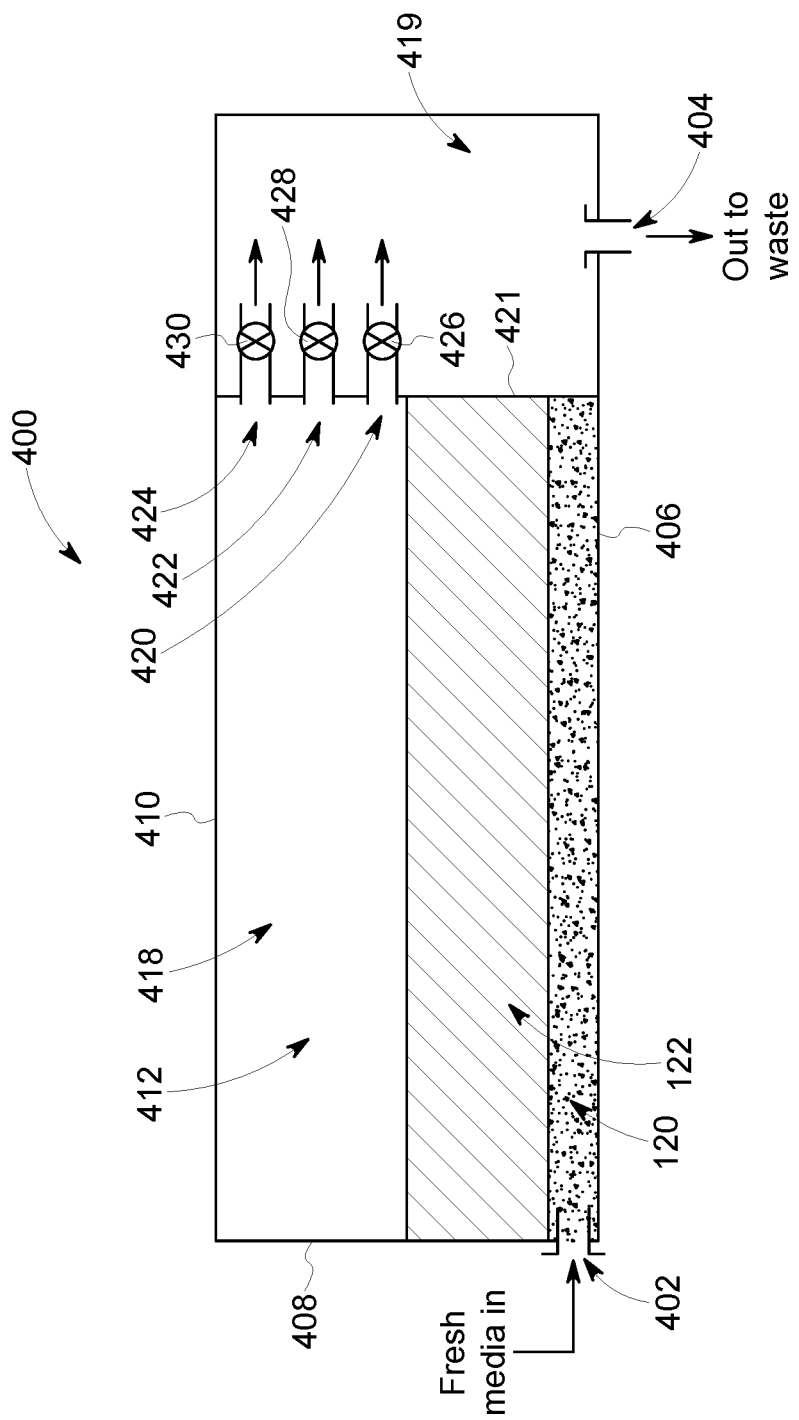
FIG. 9 is a cross-sectional view of a bioreactor vessel of the bioprocessing system of FIG. 1, according to another embodiment of the invention.

Turning finally to FIG. 9, in an embodiment, a bioreactor vessel 400 according to yet another embodiment of the invention is shown. The bioreactor vessel 400 is generally similar to the bioreactor vessel 400 of FIG. 8 and includes a bottom 406, a plurality of sidewalls 408 and a top 410 defining an interior chamber 412 therebetween. The bioreactor vessel 400 also includes an inlet/port 402 located in one of the sidewalls 408 adjacent to the bottom 406. It is contemplated, however, that in some embodiments, the inlet 402 may be located in the bottom 406 or top 410 of the bioreactor vessel 400. As shown in FIG. 9, the bioreactor vessel 400 further includes a plurality of vertically-stacked outlet ports or overflows 420, 422, 424 in either one of the sidewalls 408 or in a wall 421 dividing the interior space into a first compartment 416 for cell culturing and a second outer jacket or compartment 419, spaced different distances from the bottom 406. While FIG. 9 show three outlet ports, any number of stacked outlet ports may be employed without departing from the broader aspects of the invention. Each outlet 420, 422, 424 may be configured with a valve 426, 428, 430 (e.g., programmable valves).

In operation, the valves 426, 428, 430 may be successively opened or closed to control the media height within the bioreactor vessel 400. For example, during a first stage of cell culturing, the lowest valve 426 may be opened such that the height of the lowest outlet port 420 defines the maximum media depth. During a second stage of cell culturing, e.g., when the cell population has increased, the lowest valve 426 may be closed and the valve 428 above it may be opened. During this stage, the height of the outlet port 422 defines the maximum media depth (which is now greater than the maximum media depth when the valve 426 was open). As discussed above, by selectively opening and closing the valves 426, 428, 430 associated with each outlet 420, 422, 424, the media depth and culture volume within the bioreactor vessel 400 may be easily adjusted. Once the media overflows into the second compartment or jacket 419, it may be passively drain or pumped to waste through outlet 404.

In another embodiment, rather than using vertically-stacked valves that are each located different distances from the bottom of the bioreactor vessel and are opened or closed in dependence upon a desired media height within the bioreactor vessel, it is contemplated that the bottom of the bioreactor vessel may be lowered relative to a fixed outlet (or a single outlet) to selectively increase the media depth and volume within the bioreactor vessel.

As described above, the bioreactor vessels of the invention are much simpler than existing systems that typically require some type of reactive control logic to ensure that equivalent volumes of media are simultaneously added and removed from the bioreactor vessel during perfusion (e.g., during cell expansion). In contrast to such systems, the bioreactor vessels of the invention allow for fluid (i.e., used medium) to be removed from the top of the suspension passively by gravity through the use of a weir/wall, spill tube/outlet or siphon tube located at a predetermined height. As discussed above, this passive removal of used media minimizes the risk of aspirating cells, and largely eliminates the need for a perfusion filter to retain cells. Moreover, in embodiments where additional, fresh media is added adjacent to the bottom of the bioreactor vessel where the cells are settled, the cells have quick, immediate access to fresh nutrients as used medium is displaced upwardly over the weir or out of the outlet. In addition to the above, the depth of the suspension (i.e., cells and media) is controlled by the height of the weir or the location of the outlet. In particular, once the weir height or outlet height is set, the media depth is set. This is in contrast to existing systems where media height is usually controlled by carefully balancing the rate/volume of media in with respect to the rate/volume of media out, a much more complex procedure requiring almost constant monitoring and adjustment. The embodiments of the invention described herein therefore allow for perfusion to be implemented using fairly unsophisticated and inexpensive equipment, obviating the need for complex and costly control logic balancing media in with media out.

While the embodiments described above disclose a single culture area within the bioreactor vessel (i.e., a single first compartment for receiving a suspension containing cells and culture medium), the invention is not so limited in this regard. In particular, it is contemplated that any number of compartments may be formed within the bioreactor vessel around a central overflow chamber defined by the weir. Each of the compartments can be fed with fresh culture medium at a desired rate, and the overflow compartment is common to each of the culturing compartments. This multi-compartment format could be at the scale of a standard microplate or could be an array of larger bioreactors.

In an embodiment, a bioreactor vessel includes a first compartment configured to receive a suspension comprising cells and a cell culture medium, for use in a cell processing operation, a second compartment for receiving an overflow of the cell culture medium from the first compartment, and an overflow separating the first compartment from the second compartment, the overflow being configured to maintain a level of the cell culture medium in the first compartment. In an embodiment, the bioreactor vessel further includes an inlet associated with the first compartment and configured to direct a supply of additional cell culture medium to the first compartment. In an embodiment, the bioreactor vessel further includes an outlet associated with the second compartment and configured to allow for egress of used cell culture medium from the bioreactor vessel. In an embodiment, the overflow has a height that is less than a depth of the bioreactor vessel. In an embodiment, a maximum volume of the suspension within the bioreactor vessel is defined by the height of the overflow. In an embodiment, the height of the overflow is selectively adjustable to allow for adjustment of a depth of the suspension within the first compartment. In an embodiment, the bioreactor vessel includes a bottom, a top, and a plurality of sidewalls, the bottom, the top and the plurality of sidewalls defining an interior chamber encompassing the first compartment and the second compartment. In an embodiment, the inlet is located in the bottom of the bioreactor vessel. In an embodiment, the inlet is located adjacent to the bottom of the bioreactor vessel, in one sidewall of the plurality of sidewalls of the bioreactor vessel. In an embodiment, the bioreactor vessel additionally includes a cell-retaining membrane enclosing at least a portion of the first compartment, the cell-retaining membrane allowing for overflow of cell culture medium from the first compartment to the second compartment while retaining the cells in the first compartment. In an embodiment, the overflow is in the form of a weir configured to allow said cell culture medium to overflow the top of the weir into the second compartment.

In another embodiment, a bioprocessing system includes a bioreactor vessel having a bottom, a top and a plurality of sidewalls, the bottom, the top and the plurality of sidewalls defining an interior chamber, a weir extending upwardly from the bottom, the weir and at least one sidewall of the plurality of sidewalls defining a first compartment within the interior chamber for holding a suspension comprising cells suspended in a cell culture medium, and a second a compartment within the interior chamber for receiving an overflow of used culture medium from the first compartment, an inlet associated with the first compartment, and an outlet associated with the second compartment. The bioprocessing system further includes a first pump in fluid communication with the inlet for pumping additional cell culture medium from a media reservoir to the first compartment of the bioreactor vessel through the inlet. The outlet is configured to allow for egress of used cell culture medium from the second compartment simultaneously or near simultaneously with the pumping of the additional cell culture medium to the first compartment. In an embodiment, the system further includes a second pump in fluid communication with the outlet for pumping the used cell culture medium from the second compartment out of the bioreactor vessel. In an embodiment, the weir has a height that is less than a depth of the bioreactor vessel. In an embodiment, a maximum volume of the suspension within the bioreactor is defined by the height of the weir. In an embodiment, the height of the weir is selectively adjustable to allow for adjustment of a depth of the suspension within the first compartment. In an embodiment, the bioreactor vessel includes a cell-retaining membrane enclosing at least a portion of the first compartment, the cell-retaining membrane allowing for overflow of cell culture medium from the first compartment to the second compartment while retaining the cells in the first compartment.

In yet another embodiment, a method for bioprocessing includes the steps of, in a first compartment of a bioreactor vessel containing a suspension comprising cells suspended in a cell culture medium, introducing additional cell culture medium to simultaneously or near simultaneously cause used cell culture medium from the first compartment to exit the first compartment, wherein a substantially constant volume is maintained within the first compartment as the additional cell culture medium is introduced. In an embodiment, the bioreactor vessel includes the first compartment and a second compartment separated by a weir, wherein introducing the additional cell culture medium into the first compartment causes the used cell culture medium to flow over a top of the weir and into the second compartment. In an embodiment, the method may also include the steps of actuating a first pump to introduce the additional cell culture medium to the first compartment and actuating a second pump to remove the used cell culture medium from the bioreactor vessel, wherein the first pump is operated at least one of a different time and/or a different rate than the second pump while maintaining the substantially constant volume within the first compartment. In an embodiment, the method may also include the step of adjusting a height of the weir within the bioreactor vessel to adjust a volume of the suspension within the first compartment.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A bioreactor vessel, comprising:
   a bottom;
   a top;
   a plurality of sidewalls connecting the bottom with the top to define an interior chamber therein;
   a first compartment, disposed in the interior chamber, configured to receive a suspension comprising cells and a cell culture medium, for use in a cell processing operation, wherein the first compartment abuts each of the plurality of sidewalls;
   a second compartment, disposed in the interior chamber about the first compartment, for receiving an overflow of used cell culture medium from the first compartment, wherein the second compartment is surrounded entirely by the first compartment and spaced apart from the plurality of sidewalls;
   an inlet in fluid communication with the interior chamber to receive fresh cell culture medium that is supplied to the first compartment;

an overflow separating the first compartment and the second compartment, the overflow configured to allow for passage of the used cell culture medium from the first compartment to the second compartment when the level of cell culture medium within the first compartment exceeds a height of the overflow to maintain a level of the cell culture medium in the first compartment at a height equal to or less than the height of the overflow, the amount of used cell culture medium passing over the overflow from the first compartment into the second compartment corresponds to the amount of fresh cell culture medium supplied to the first compartment from the inlet, wherein a volume of fresh cell culture medium added to the first compartment at a predetermined rate causes an equivalent volume of used cell culture medium to pass over the overflow into the second compartment at the same predetermined rate, maintaining a constant volume of cell culture medium in the first compartment; and an outlet associated with the second compartment and configured to receive the used cell culture medium passing over the overflow for passage out of the bioreactor vessel;

wherein the height of the overflow is selectively adjustable to allow for adjustment of a depth of the suspension within the first compartment.

2. The bioreactor vessel of claim 1, wherein:
the inlet is located in one of the plurality of sidewalls adjacent to the bottom.

3. The bioreactor vessel of claim 1, wherein:
the overflow has a height that is less than a depth of the bioreactor vessel.

4. The bioreactor vessel of claim 1, wherein:
a maximum volume of the suspension within the bioreactor vessel is defined by the height of the overflow.

5. The bioreactor vessel of claim 1, wherein:
the second compartment is generally conical or funnel-shaped.

6. The bioreactor vessel of claim 1, wherein:
the inlet is located in the bottom of the bioreactor vessel.

7. The bioreactor vessel of claim 1, further comprising:
a cell-retaining membrane enclosing at least a portion of the first compartment, the cell-retaining membrane allowing for overflow of the used cell culture medium from the first compartment to the second compartment while retaining the cells in the first compartment.

8. The bioreactor vessel of claim 1, wherein:
the overflow comprises a weir configured to allow the used cell culture medium to overflow the top thereof into the second compartment.

9. The bioreactor vessel of claim 1, wherein:
the overflow includes a plurality of vertically-spaced outlets, each outlet having a control valve associated therewith for selectively preventing or allowing a flow of the cell culture medium out of said outlet.

10. A bioreactor vessel, comprising:
a bottom;
a top;
a plurality of sidewalls connecting the bottom with the top to define an interior chamber therein;
a first compartment, disposed in the interior chamber, configured to receive a suspension comprising cells and a cell culture medium, for use in a cell processing operation;
a second compartment, disposed in the interior chamber about the first compartment, for receiving an overflow of used cell culture medium from the first compartment;
an overflow separating the first compartment and the second compartment, the overflow being configured to allow for passage of the used cell culture medium from the first compartment to the second compartment when the level of cell culture medium within the first compartment exceeds a height of the overflow to maintain a level of the cell culture medium in the first compartment at a height equal to or less than the height of the overflow; and
an outlet associated with the second compartment and configured to receive the cell culture medium passing over the overflow and to allow for passage of the cell culture medium passing over the overflow out of the bioreactor vessel;
wherein the overflow includes a plurality of vertically-spaced outlets extending between the top and the bottom, each outlet having a control valve associated therewith for selectively preventing or allowing a flow of the cell culture medium out of said outlet.

11. The bioreactor vessel of claim 8, wherein the overflow is configured for extendable and retractable movement within the interior chamber in relation to the bottom.

12. The bioreactor vessel of claim 1, wherein the outlet is located in one of the bottom, the top, and a sidewall of the plurality of sidewalls.

13. The bioreactor vessel of claim 10, wherein each of the vertically-spaced outlets and corresponding control valves is operated as a function of cell culturing in the first compartment.

14. The bioreactor vessel of claim 13, wherein at an initial stage of cell culturing a vertical outlet and corresponding control valve that is closest to the bottom is opened and in fluid communication with the outlet associated with the second compartment while the other vertical outlets and corresponding controls valves vertically above are closed.

15. The bioreactor vessel of claim 14, wherein at a subsequent stage of cell culturing during which cell population increases, the vertical outlet and corresponding control valve immediately above the previously opened vertical outlet and corresponding control valve is opened and in fluid communication with the outlet while the other vertical outlets and corresponding controls valves are closed.

16. The bioreactor vessel of claim 15, wherein the vertical outlets and corresponding control valves closer towards the top are opened as the cell population in the first compartment increases.

* * * * *